(12) United States Patent
Smith et al.

(10) Patent No.: US 9,687,203 B2
(45) Date of Patent: Jun. 27, 2017

(54) METHOD AND APPARATUS FOR TABLE-GANTRY ALIGNMENT IN AN IMAGING SYSTEM

(71) Applicant: General Electric Company, Schenectady, NY (US)

(72) Inventors: Brandon Allan Smith, Waukesha, WI (US); Ariel Friedlander, Mequon, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 212 days.

(21) Appl. No.: 14/573,125

(22) Filed: Dec. 17, 2014

(65) Prior Publication Data

US 2016/0174929 A1  Jun. 23, 2016

(51) Int. Cl.
*A61B 6/04* (2006.01)
*A61B 6/03* (2006.01)

(52) U.S. Cl.
CPC ............ *A61B 6/0492* (2013.01); *A61B 6/035* (2013.01)

(58) Field of Classification Search
CPC ........... A61B 6/00; A61B 6/032; A61B 6/035; A61B 6/04; A61B 6/0407; A61B 6/0428; A61B 6/0457; A61B 6/0492; A61B 6/589; A61N 5/1049
USPC ................................... 378/20, 204, 205, 206
See application file for complete search history.

(56) References Cited

U.S. PATENT DOCUMENTS

| 6,917,666 B2 | 7/2005 | Wollenweber |
| 2013/0329217 A1* | 12/2013 | Yan ........................ G01B 11/26 356/138 |

* cited by examiner

*Primary Examiner* — Jurie Yun
(74) *Attorney, Agent, or Firm* — Fletcher Yoder, P.C.

(57) ABSTRACT

Method and apparatus are provided for aligning a cradle supported by a table in an imaging system with a gantry scan plane in a bore of the gantry. More particularly, various embodiments provide a laser alignment structure having at least two alignment apertures arranged along an axis of the bore, and an adjustment device configured to adjust a position of the laser so that the laser beam is aligned with the alignment apertures. Highly accurate alignment of the cradle to the gantry scan plane is achieved by utilizing this apparatus in tandem with an imaging-based alignment analysis method.

18 Claims, 6 Drawing Sheets

METHOD AND APPARATUS FOR TABLE-GANTRY ALIGNMENT IN AN IMAGING SYSTEM

BACKGROUND

An increase in the precision of medical imaging systems has led to a need for more precise alignment of components of the imaging systems, including more precise alignment of the table to a scan plane. Misalignment of the table relative to the scan plane may negatively affect image quality or introduce imaging artifacts. In Computed Tomography (CT) systems, for example, various laser devices are used to align the table to the scan plane of the gantry bore. Misalignment of the lasers may affect the correct alignment of the table to the gantry scan plane of the imaging system. This misalignment may affect image quality. Current laser alignment procedures are dependent upon an operator centering a laser beam of a stationary laser using a target. These procedures are time-consuming and are susceptible to misalignment due to operator error and/or inaccuracies in the target. Much time is required to correct misalignment of the table to the gantry scan plane.

BRIEF DESCRIPTION OF THE INVENTION

In accordance with various embodiments, an imaging system is provided that includes a gantry having a bore, a table including a portion having alignment marks, a laser provided in a laser housing, and a laser alignment structure. The laser alignment structure is arranged relative to the gantry bore and supports the laser, which emits a laser beam. It further includes at least one alignment aperture arranged along an axis of the bore, and an adjustment device to adjust the position of the laser so that the laser beam is aligned with the alignment aperture.

In accordance with various embodiments, a method for aligning a portion of a table to a gantry scan plane is provided that includes emitting a laser beam along an axis of a bore of the gantry toward at least one aperture arranged along the axis of the bore in a laser alignment structure that is arranged proximate to the bore of an imaging system. The position of the laser on the laser alignment structure is adjusted to align the laser beam from the laser with the aperture such that the laser beam passes through the aperture onto the portion of the table, which includes alignment marks. The position of the table is adjusted to align the laser beam passing through the aperture with the alignment marks so that the portion of the table is aligned with the gantry scan plane of the imaging system.

DETAILED DESCRIPTION OF THE INVENTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

"Systems," "units," or "modules" may include or represent hardware and associated instructions (e.g., software stored on a tangible and non-transitory computer readable storage medium, such as a computer hard drive, read only memory (ROM), random access memory (RAM), dynamic RAM or DRAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "image" or similar terminology is not intended to exclude embodiments in which data representing an image is generated, but a viewable image is not. Therefore, as used herein the term "image" broadly refers to both viewable images and data representing a viewable image. However, certain embodiments generate, or are configured to generate, at least one viewable image.

Various laser devices may be used to align the table to the scan plane of an imaging system, such as a CT system, for example. Various embodiments disclosed herein provide systems and methods for aligning a portion of a table or a cradle supported by a table in an imaging system with a gantry scan plane or axes of a bore of the gantry. In general, the axes of the gantry of an imaging system are based upon a theoretical point of origin that is unique to each gantry based on manufacturing tolerances. Accurate alignment of the table to this point of origin is achieved by a laser-based alignment apparatus and method as disclosed herein. Confirmation of the table alignment is conducted using an imaging-based analysis method. By enabling highly accurate initial table positioning with the laser apparatus, minimal or no corrections in table orientation may be required after feedback from the imaging-based analysis method.

More particularly, various embodiments provide a laser alignment structure having at least two alignment apertures arranged along an axis of the bore, and an adjustment device configured to adjust a position of the laser so that the laser beam is aligned with the alignment apertures. The laser beam passes through the apertures onto the cradle that includes alignment marks. The cradle is aligned with a gantry scan plane of the imaging system by positioning the cradle such that the alignment marks of the cradle align with the laser beam passed through the two apertures. Embodiments disclosed herein provide highly accurate alignment of the cradle and the gantry scan plane by utilizing at least two apertures for more accurate laser alignment and an adjustment mechanism that enables adjustment of the position of the laser to accurately align with the apertures.

According to various embodiments, a laser is used for alignment of the cradle of the imaging system, where the position of the laser itself is adjustable in multiple degrees of freedom on a laser alignment structure for high accuracy alignment. The laser alignment apparatus mounts to the gantry rotating structure and provides an interface to attach a readily-available construction laser. The laser alignment structure includes an adjustment mechanism that enables the position of the laser to be adjusted on the laser alignment apparatus to align it to at least two apertures provided in the laser alignment structure. This eliminates tolerance stack-up within the laser housing and enables usage of an inexpensive, off-the-shelf construction laser. The laser beam from the laser shines onto the table cradle to enable alignment of the cradle to the laser. The table is moved on the floor to align the cradle with the laser beam. In some embodiments, the laser alignment structure may be mounted to the same dowel pin holes that are used for aligning the gantry lasers.

The laser alignment structure according to various embodiments disclosed herein enables reduced installation time through very close table alignment with the gantry scan plane. This reduces the necessity for re-alignment upon final software checks, and/or reduces the amount of table movement required (e.g., manual repositioning) to satisfy the final software checks. More particularly, the table is anchored to the floor at the end of all software alignment checks because of the risk that the anchors were installed too far from the final position (e.g., due to inadequate initial hardware alignment). However, with the highly accurate alignment provided by embodiments disclosed herein, the table may be securely anchored earlier in the installation process. This enables reduced overall installation time.

It should be noted that although various embodiments are described in connection with a CT imaging systems having particular components, including specific configurations or arrangements, the various embodiments are not limited to CT imaging systems. Accordingly, the various embodiments may be implemented in connection with any type of imaging system, for example, medical diagnostic imaging (e.g., X-ray system), non-destructive imaging, etc.

Figure 1:
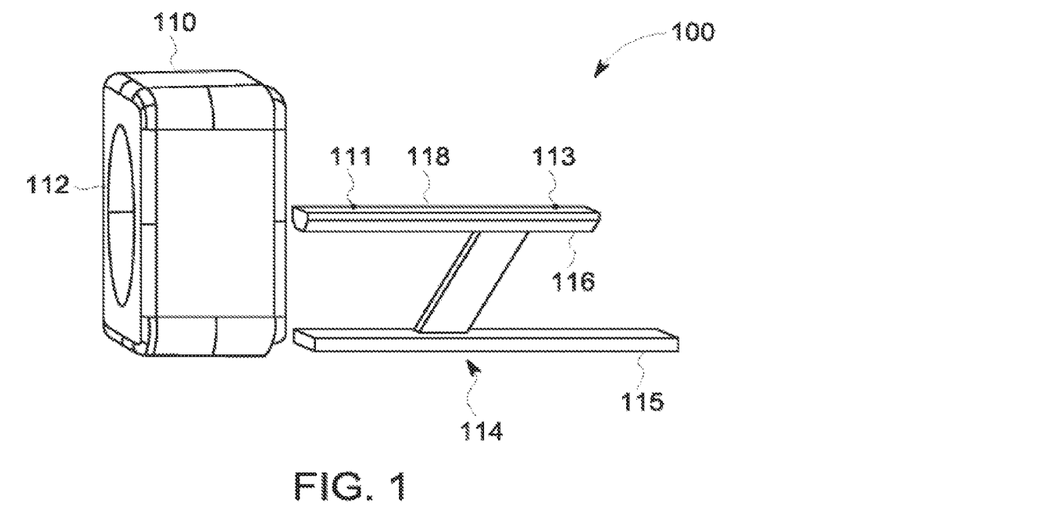
FIG. 1 is a perspective view of an exemplary imaging system constructed in accordance with various embodiments.

FIG. 1 is a perspective view of an imaging system in accordance with an embodiment of the invention. The imaging system 100 includes a gantry 110, table 114, and an operator workstation (not shown). The operator workstation typically commands and controls the processes and mechanical operation of the imaging system. Gantry 110 has a bore 112 formed therein. Table 114 includes a base 115, a cradle 118 and a table upper structure 116. The cradle 118 and the table upper structure 116 are arranged such that the cradle may be translated or moved into the bore 112 such that a patient resting on the cradle can be scanned. Table 114 can typically be controlled to change the front and/or rear elevation of the cradle 118 and/or the table upper structure 116 can be adjusted to alter the height of the cradle 118, for example.

Figure 2:
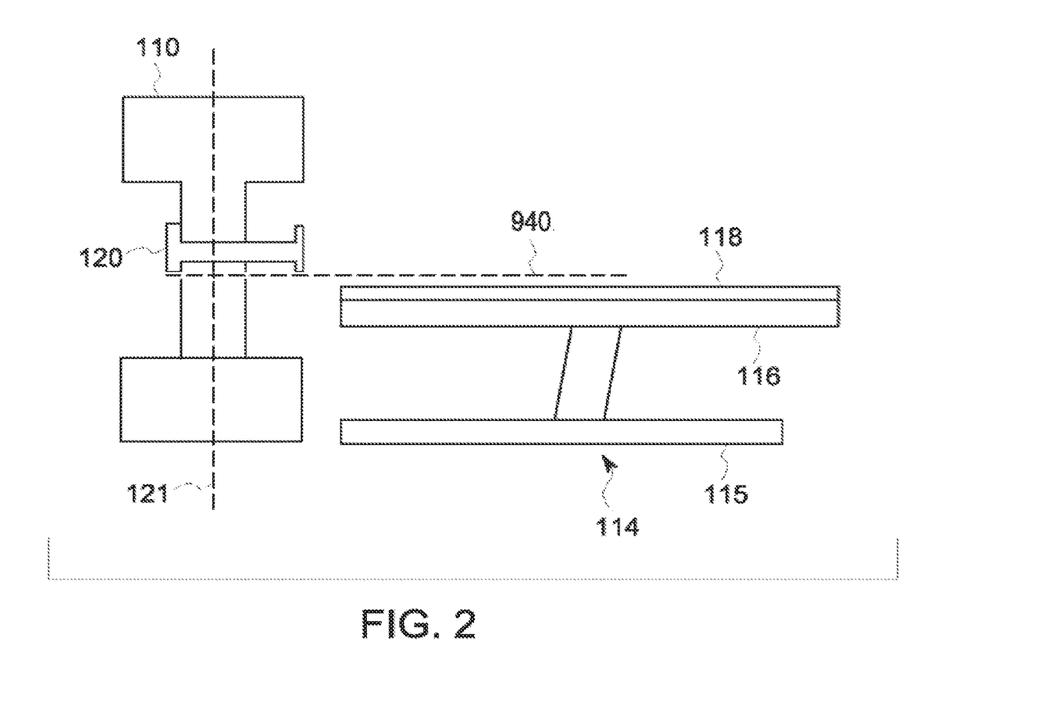
FIG. 2 is a side view of an imaging system constructed in accordance with various embodiments.

FIG. 2 is a side view of the imaging system shown in FIG. 1 including a laser alignment apparatus according to various embodiments. As shown in FIG. 2, a laser alignment structure 120 is mounted to the gantry 110 of the imaging system 100. Any suitable mounting mechanism may be used to mount the laser alignment structure 120 to the gantry 110. The mounting mechanism may be permanent or allow for removal of the laser alignment structure 120. The laser alignment structure 120 is positioned on the gantry 110 above the cradle 118 to enable the cradle 118 to move in and out of the bore 112. The laser alignment structure 120 enables highly accurate alignment of the cradle 118 to the gantry scan plane 121.

Figure 3:
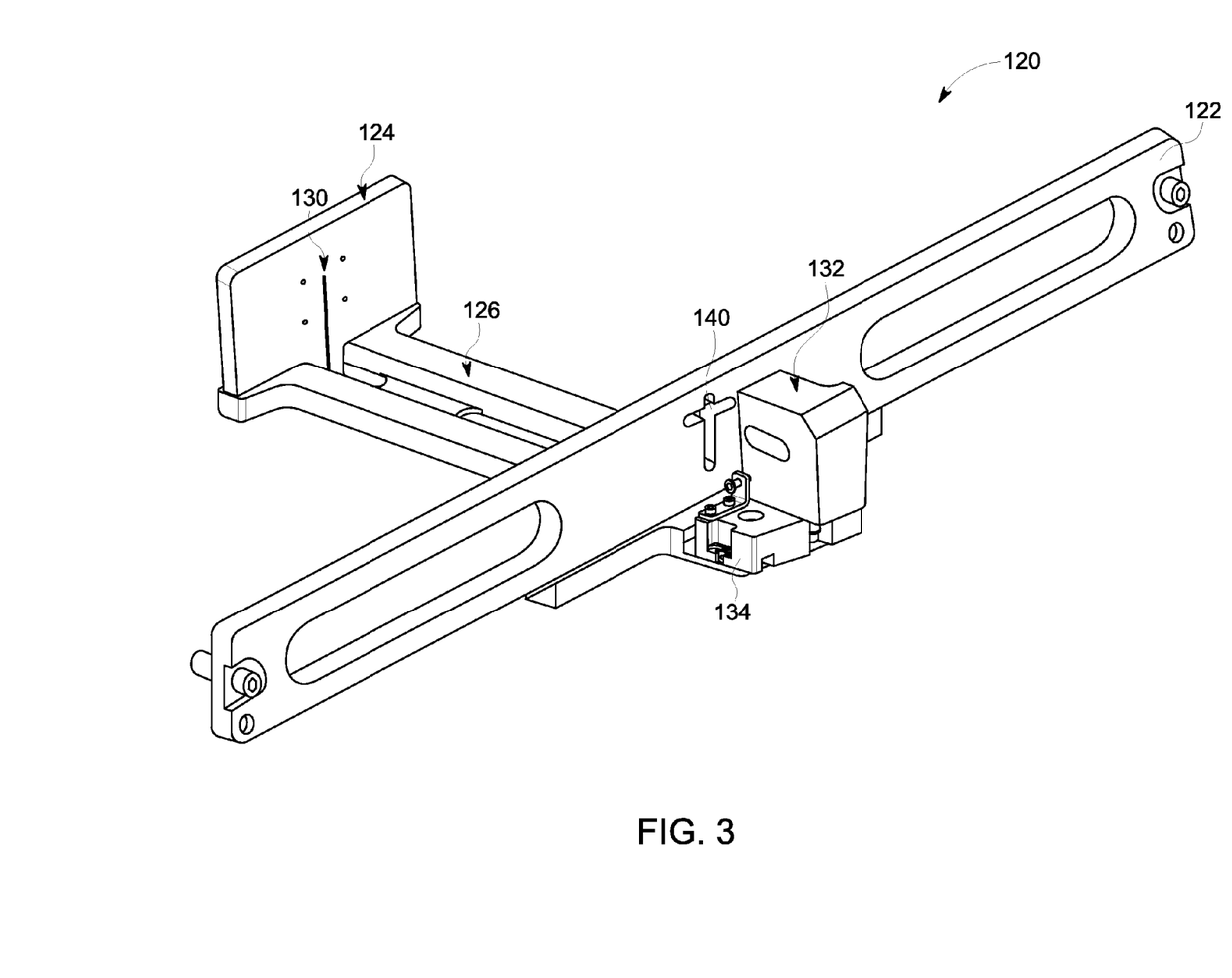
FIG. 3 is a schematic view of a laser alignment structure in accordance with various embodiments.

Referring to FIG. 3, a laser alignment structure 120 according to various embodiments is shown. The laser alignment structure 120 includes a main crossbar 122 having an aperture 140, a target 124 having another aperture 130, a support structure 126, a laser 132, and an adjustment mechanism 134. In some embodiments, the laser alignment structure 120 is mounted to the rear face of the rotating gantry 110 via the main crossbar 122. However, the laser alignment structure 120 may be mounted in any manner suitable to enable laser alignment of the cradle 118 with the gantry scan plane 121. The length of the support structure 126, or the distance between the apertures 140 and 130, may be set to any suitable distance depending upon the imaging system and arrangement of the laser alignment structure 120. The main crossbar 122, target 124 and support structure 126 may be separate elements that are secure together by some suitable means such as bolts, for example, or may be formed as a single structure. The main crossbar 122, the target 124 and the support structure 126 may be formed of any suitable material such as metal, for example. The laser alignment structure 120 may be mounted using the same fixture holes that are used to align the gantry imaging alignment laser lights.

Figure 4A:
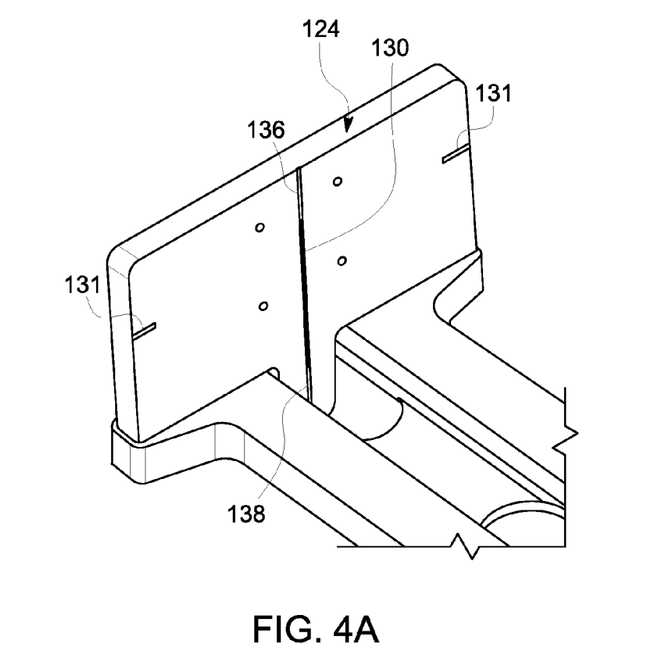
FIGS. 4A and 4B are schematic views of alignment apertures of the laser alignment structure shown in FIG. 3 in accordance with various embodiments.
Figure 4B:
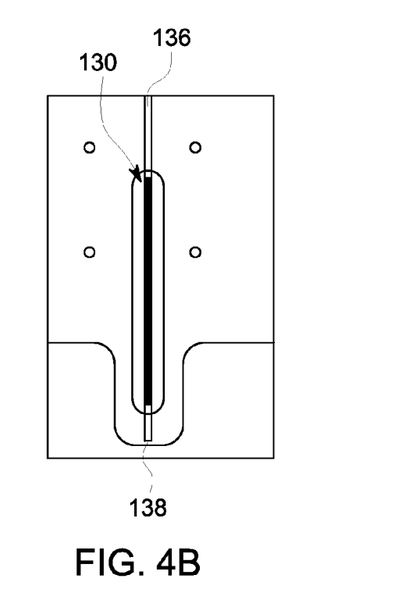
Figure 5:
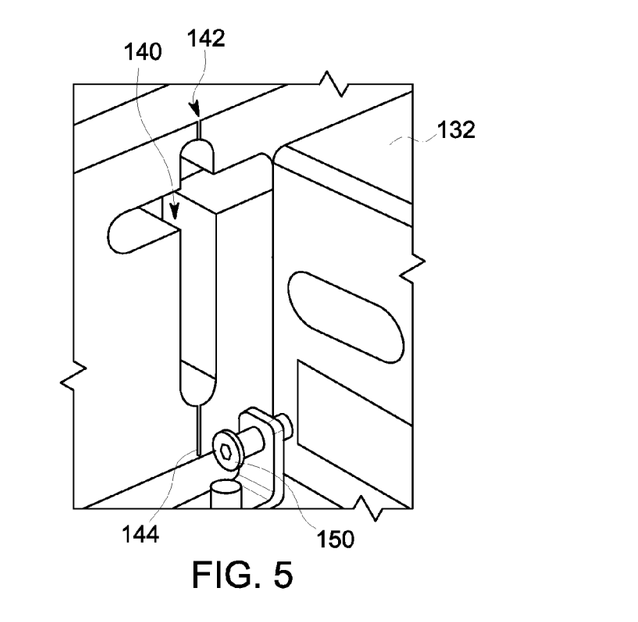
FIG. 5 is a schematic view of an aperture of the laser alignment structure shown in FIG. 3 in accordance with various embodiments.

The first or primary aperture 140 and the second or secondary aperture 130 are provided to shine the laser beam through to the table cradle 118. Aperture 140 enables a laser beam produced in multiple directions to be used to align the cradle 118 to the gantry scan plane 121. According to various embodiments, the laser is aligned in two axes, translation in X and rotation about Y, to the primary and secondary apertures 140, 130 using the adjustment device 134, described in more detail below. The laser alignment structure 120 also includes recess slots 136 and 138 arranged above and below the aperture 130, respectively, as shown in FIGS. 4A and 4B, and recess slots 142 and 144 arranged above and below the aperture 140, respectively, as shown in FIG. 5. The recessed slots 136, 138, 142 and 144 facilitate visual alignment of the laser beam to the center of the associated apertures 130 and 140. In some embodiments, the apertures 130 and 144 are sized to match the laser beam so that any misalignment is apparent to the operator.

In various embodiments, the laser 132 generates a fan beam and the laser 132 is positioned, via the adjustment device 134, to align the laser beam in the YZ plane with the recess slots 142 and 144 of the aperture 140, and to further align the laser beam in the YZ plane with the recess slots 136 and 138 of the aperture 130. The aperture 140 also allows a laser beam in the XZ plane to pass through it toward target 124. The recess slots 131 on target 124 allow for a laser XZ plane with self-leveling beam to indicate how level the apparatus is to the horizontal plane.

Figure 6:
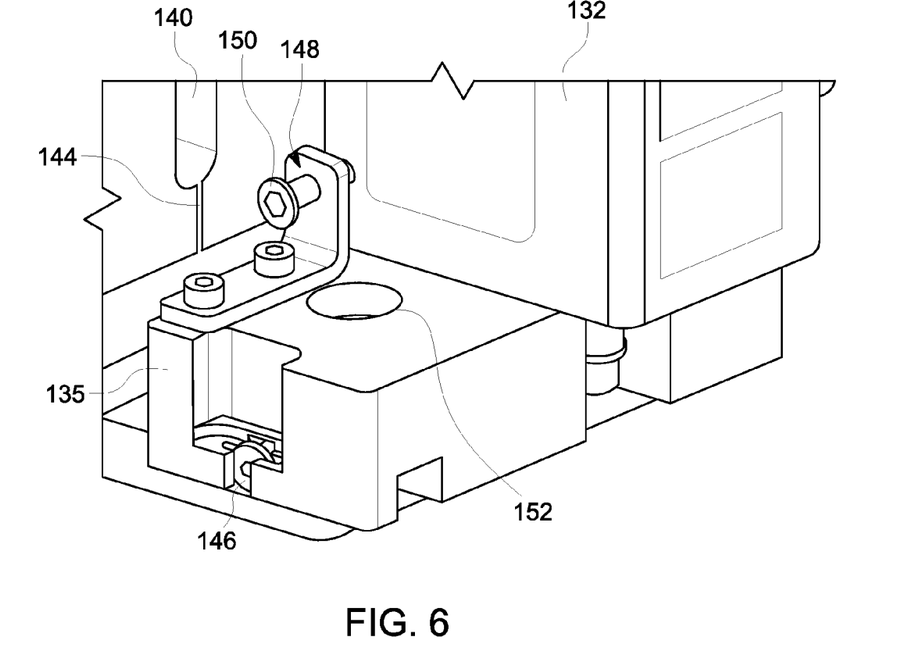
FIG. 6 is a schematic view an adjustment device in accordance with various embodiments.
Figure 7:
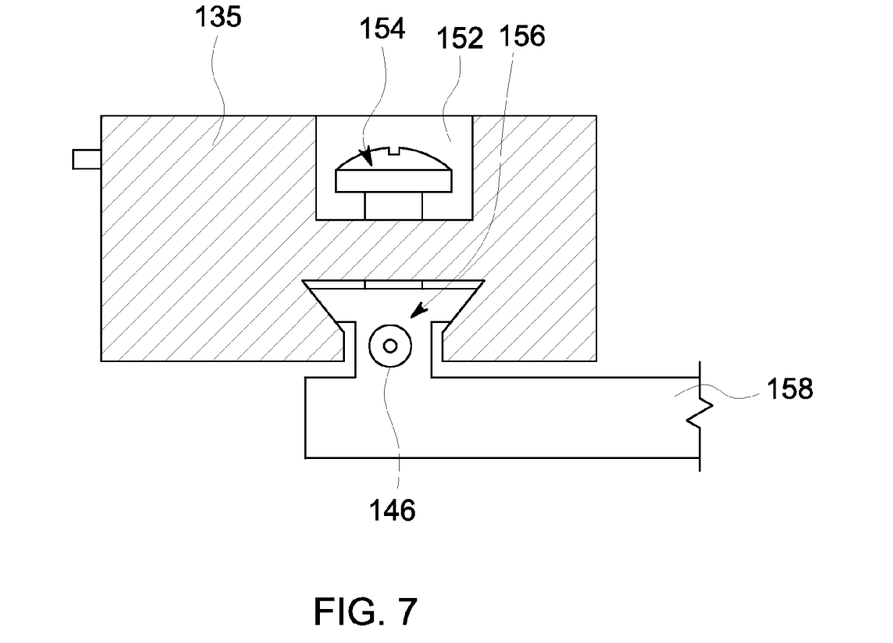
FIG. 7 is a cross-sectional view of the adjustment device shown in FIG. 6.

Referring to FIGS. 6 and 7, an exemplary embodiment of the adjustment device 134 is shown. The adjustment device 134 enables the position of the laser 132 to be adjusted in the X and Y directions to align the laser with the apertures 140 and 130. The adjustment device 134 includes a slider block 135 that is arranged on a bracket that is secured to or formed as part of the laser alignment structure 120. The slider block 135 of the adjustment device 134 is arranged to translate the laser 132 back and forth along an X axis. According to the embodiment shown, the X translation adjustment is provided by a dovetail 156 arranged on a bracket 158 that may be separate or formed as part of the laser alignment structure 120, a jackscrew 146, and 2 nylon screws 154 (only one shown in Figure, the other being located under the laser housing), one being arranged in opening 152 to remove mechanical slop from the motion between the slider block 135 and the structure 120. The nylon screws 154 preload the dovetail 156 to be tight against the angled surfaces (removing gaps), and the plastic screw material allows the parts to slide against the screws 154. Torquing the plastic screws 154 makes the dovetail 156 angled surfaces evenly contact a corresponding angle of a recess in the slider block 135. This enables smooth motion and the ability for friction to hold the parts in place.

Figure 8:
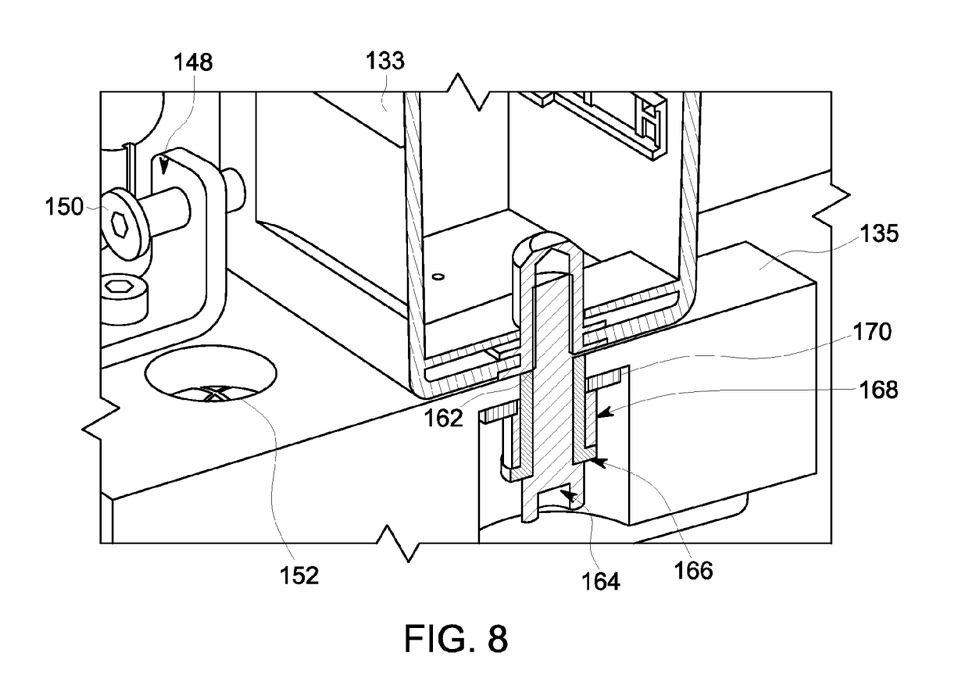
FIG. 8 is a cross-sectional view of a laser housing and the laser alignment structure arranged in accordance with various embodiments.

Referring to FIGS. 6 and 8, the Y axis rotational adjustment according to an exemplary embodiment is provided by a jackscrew 150 on the side of the laser housing 133 of the laser 132, and a spring 168 on a laser mounting hole 162 arranged in the laser housing 133 to provide motion resistance and retention of the laser 132. The motion resistance is needed for smooth operation of the jackscrew 150 to avoid jerking of the laser 132. The mounting hole 162 operates like a pivot. In some embodiments, the jackscrew 150 is supported by joint structure 148 that is arranged on or formed as part of the laser alignment structure 120. In various embodiments, the laser housing 133 is mounted to the slider block 135 via a mounting bolt 164 through the laser mounting hole 162, a bushing 166, the spring 168, and washer 170, as shown in FIG. 8. The mounting bolt 164 locks the bushing 166 to the laser housing 133. The laser 132 and the bushing 166 are able to rotate relative to the slider block 135. The spring 168 provides some resistance to movement (frictional force) so that motion is smooth.

The apertures 140 and 130 allow light to shine through to the cradle 118. Once the operator visually aligns the laser beam with the recessed slots 142, 144 of aperture 140 and recessed slots 136 and 138 of aperture 130, the laser beam shines onto the table cradle 118, to illuminate the front and rear center lines or alignment marks 111 and 113, shown in FIG. 1, that are provided on the cradle 118. Any number of alignment marks can be included on the cradle 118. The laser shines on the cradle surface which allows the cradle 118 to be moved in/out of the gantry bore 112. The laser alignment structure 120 is positioned above the cradle 118 so that this in/out motion is possible. The in/out cradle motion ensures that the cradle 118 is aligned to the scan plane 121 through its range of travel in addition to the fully retracted home position. The laser light shines on the cradle with significant margin to enable other devices, such as laser targets, to be positioned if desired.

According to various embodiments, once the laser 132 is aligned with the gantry scan plane 121 using the laser alignment structure 120, software or image-based alignment may be performed to verify the accuracy of the alignment.

Figure 9:
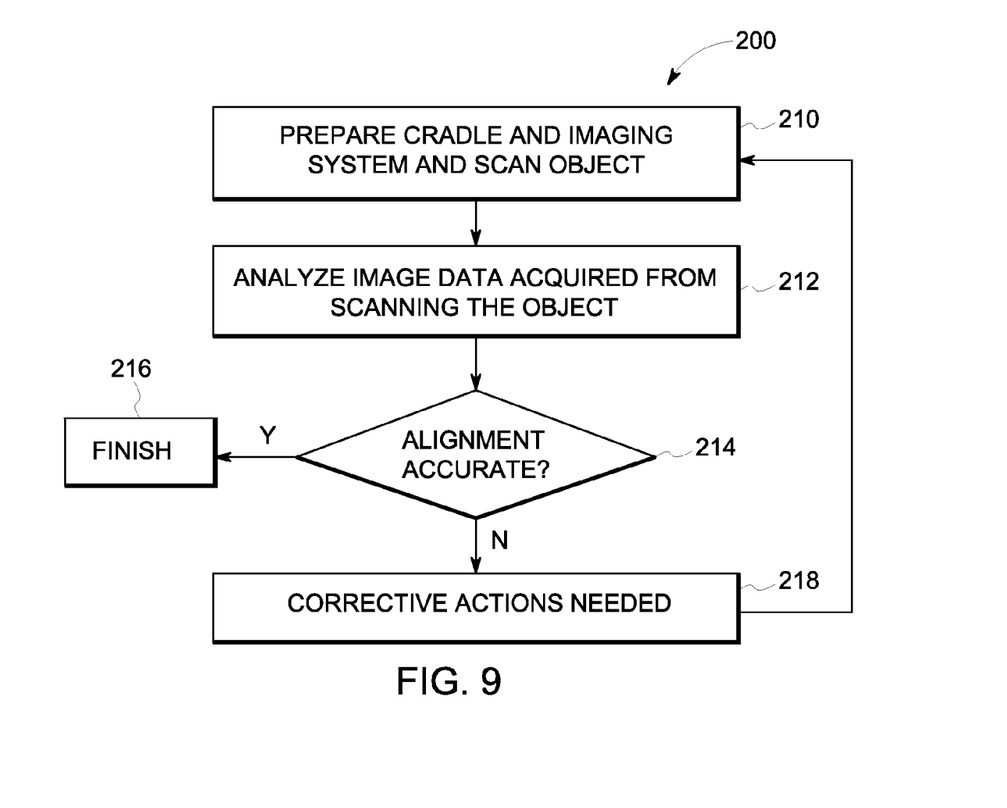
FIG. 9 is a flowchart of an exemplary process for verifying accuracy of alignment in accordance with various embodiments.

FIG. 9 is a flowchart of another exemplary process for verifying the accuracy of the alignment using the laser alignment structure 120. The process 200 includes preparing the cradle 118 and imaging system and scanning an object in step 210. Preparing the cradle 118 may include removing extraneous objects or elements or any other suitable preparation. In step 212, the image data generated by scanning the object are analyzed to verify that the cradle 118 is accurately aligned with the gantry scan plane 121. If it is determined in step 214 that the alignment is accurate, then the process finishes in step 216. If the alignment is not accurate in step 214, then corrective actions are provided in step 218. Once the corrective actions have been taken, the process is repeated at step 210. In various embodiments, the process for verifying the accuracy of the alignment may be performed by a system computer of the imaging system.

Figure 10:
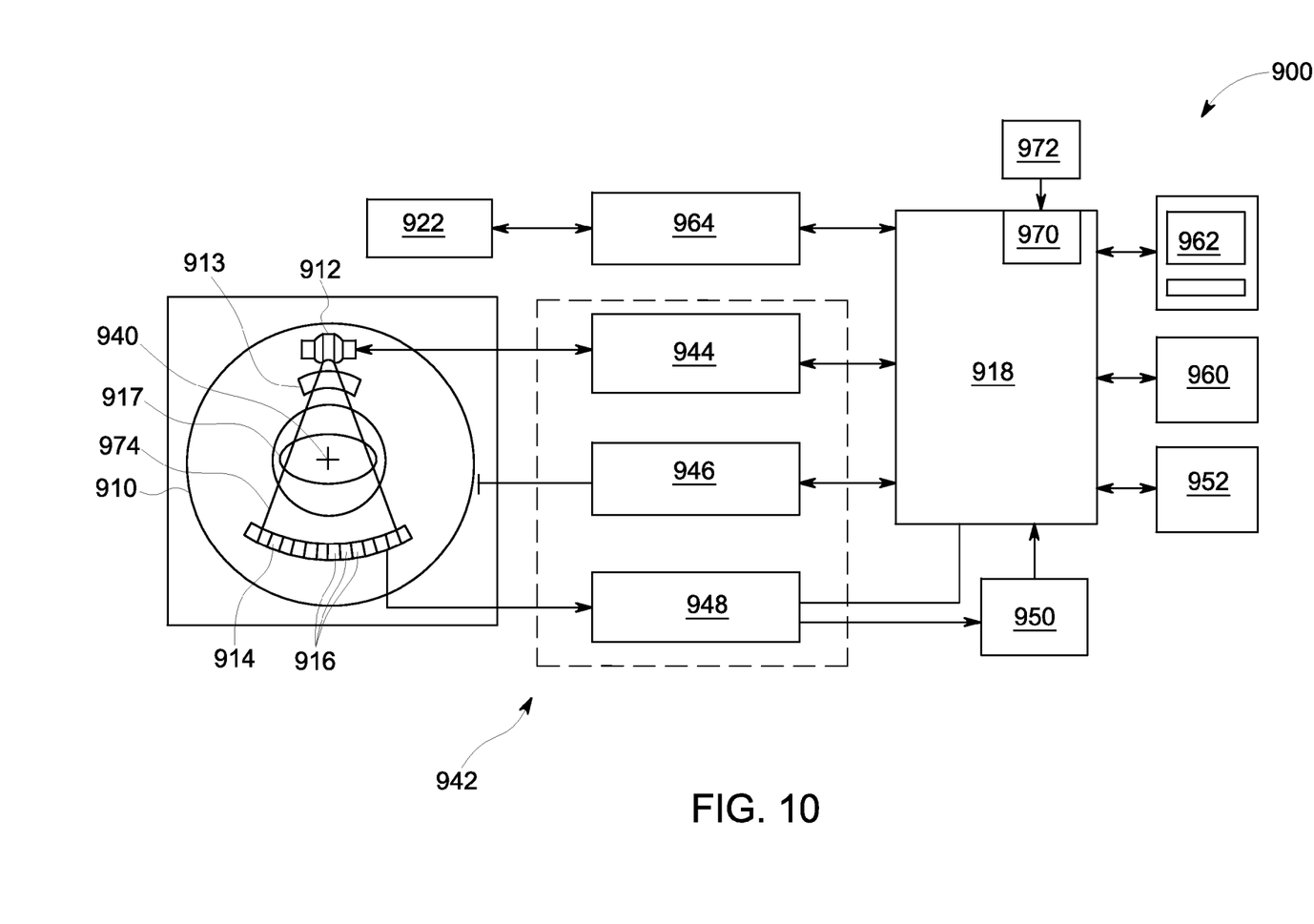
FIG. 10 is a block diagram of an imaging system in accordance with various embodiments.

Various methods and/or systems (and/or aspects thereof) described herein may be implemented using a medical imaging system. For example, FIG. 10 is a block schematic diagram of an exemplary CT imaging system 900 that may be utilized to implement various embodiments discussed herein. The CT imaging system 900 includes a gantry 910 that has an X-ray source 912 that projects a beam of X-rays toward a detector array 914 on the opposite side of a gantry 910. A source collimator 913 is provided proximate the X-ray source 912. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

As discussed above, the detector 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 9 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab corresponding to a 360 degree view may be obtained using less than a complete revolution.

Thus, according to various embodiments, a laser alignment structure is provided which includes at least two alignment apertures arranged along an axis of the bore, and an adjustment device configured to adjust a position of the laser so that the laser beam is aligned with the alignment apertures. The laser beam passes through the apertures onto the cradle that includes alignment marks. The cradle is aligned with a gantry scan plane of the imaging system by positioning the cradle such that the alignment marks of the cradle align with the laser beam passed through the two apertures. Embodiments disclosed herein provide highly accurate alignment of the cradle and the gantry scan plane by utilizing at least two apertures for more accurate laser alignment and an adjustment mechanism that enables adjustment of the position of the laser to accurately align with the apertures. The position of the laser itself is adjustable in multiple degrees of freedom on a laser alignment structure for high accuracy alignment. The laser alignment apparatus mounts to the gantry rotating structure and provides an interface to attach a readily-available construction laser.

It is to be understood that the above description is intended to be illustrative, and not restrictive. For example, specific embodiments of the adjustment device, slider block, and laser 132 arrangements are shown, however, it is to be understood that the arrangements shown herein are intended to be illustrative and not restrictive. Variations in arrangement and assembly of the various elements disclosed in embodiments herein may be apparent to those skilled in the art and such modifications may be made without departing from the scope of the various embodiments. The above-described embodiments (and/or aspects thereof) may be used in combination with each other. In addition, many modifications may be made to adapt a particular situation or material to the teachings of the various embodiments of the invention without departing from their scope. Many other embodiments will be apparent to those of skill in the art upon reviewing the above description. The scope of the various embodiments of the invention should, therefore, be determined with reference to the appended claims, along with the full scope of equivalents to which such claims are entitled.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:
1. An imaging system, comprising:
a gantry including a bore;
a table including a portion having alignment marks;
a laser having a laser housing and configured to emit a fan-shaped laser beam along an axis of the bore; and
a laser alignment structure supporting the laser and mounted relative to the gantry bore so that the laser, when operated, emits the fan-shaped laser beam in a vertical (YZ) plane relative to the bore, the laser alignment structure having at least one alignment aper- ture arranged along the axis of the bore through which the fan-shaped laser beam passes and, when in alignment, is incident upon the alignment marks, and having an adjustment device configured to adjust a position of the laser so that the fan-shaped laser beam is aligned with the at least one alignment aperture, wherein each alignment aperture is slot-shaped to allow the fan-shaped laser beam to pass through.

2. The imaging system of claim 1, wherein the laser alignment structure is coupled to the gantry.

3. The imaging system of claim 1, wherein the laser alignment structure comprises at least two alignment apertures.

4. The imaging system of claim 3, wherein the at least two alignment apertures are separated by a predetermined distance and comprise a primary aperture and a secondary aperture, wherein the primary aperture is arranged proximate to the laser.

5. The imaging system of claim 4, wherein the primary aperture is larger than the secondary aperture.

6. The imaging system of claim 3, wherein the laser alignment structure further comprises recessed slots arranged above and below the at least two alignment apertures, respectively, wherein the recessed slots enable visual alignment of the laser beam with the at least two alignment apertures.

7. The imaging system of claim 1, wherein the portion of the table comprises a cradle.

8. The imaging system of claim 1, wherein the laser beam passes through the at least one alignment aperture onto the portion and the portion is aligned with a gantry scan plane by positioning the portion such that the alignment marks align with the laser beam passed through the at least one alignment aperture.

9. The imaging system of claim 1, wherein the laser alignment structure further comprises recessed slots arranged above and below the at least one alignment aperture, wherein the recessed slots enable visual alignment of the laser beam with the at least one alignment aperture.

10. The imaging system of claim 9, wherein the recessed slots are sized to match a size of the fan-shaped laser beam from the laser.

11. The imaging system of claim 1, wherein the laser alignment structure is arranged above the portion of the table to enable movement of the portion in and out of the bore of the gantry.

12. The imaging system of claim 1, wherein the laser alignment structure comprises a crossbar that is mounted to a rear side of the gantry.

13. The imaging system of claim 1, wherein the adjustment device comprises a sliding support having a translation adjuster and a rotation adjuster to align the laser to the at least one alignment aperture, wherein the sliding support supports the laser and the laser housing.

14. The imaging system of claim 13, wherein the translation adjuster comprises jackscrews impinging upon opposing sides of a dovetail of the laser alignment structure engaged with the sliding support, and at least one screw arranged in an opening of the sliding support and perpendicular to the dovetail and further arranged to come into contact with the dovetail.

15. The imaging system of claim 13, wherein the rotation adjuster comprises a jackscrew impinging upon a side of the laser housing and a spring arranged about a bushing of a bolt that secures the laser housing to the sliding support.

16. The imaging system of claim 1, wherein the laser alignment structure is metal.

17. A method, comprising:
emitting, from a laser supported by a laser alignment structure mounted relative to a bore of a gantry of an imaging system, a fan-shaped laser beam along an axis of the bore of the gantry toward an aperture arranged along the axis of the bore in the laser alignment structure mounted to the gantry, wherein the aperture is slot-shaped to allow the fan-shaped laser beam to pass through;
adjusting a position of the laser on the laser alignment structure to align the fan-shaped laser beam with the aperture such that the fan-shaped laser beam passes through the aperture onto a portion of a table in the imaging system, wherein the portion comprises alignment marks; and
adjusting a position of the portion of the table to align the fan-shaped laser beam passing through the aperture with the alignment marks to align the portion of the table with a gantry scan plane of the imaging system.

18. The method of claim 17, further comprising visually aligning the laser beam to recess slots arranged above and below the aperture of the laser alignment structure.

* * * * *